United States Patent
Gayoso Babío et al.

(10) Patent No.: US 10,370,704 B2
(45) Date of Patent: Aug. 6, 2019

(54) MUTATION IDENTIFICATION METHOD

(71) Applicant: HEALTH IN CODE, S.L., As Xubias (La Coruña) (ES)

(72) Inventors: Carmen María Gayoso Babío, As Xubias (ES); Óskar Martínez De Ilárduya Ruiz De Larramendi, As Xubias (ES); Iván Aarón Lesende Rodríguez, As Xubias (ES)

(73) Assignee: HEALTH IN CODE, S.L., As Xubias (La Coruna) (ES)

( * ) Notice: Subject to any disclaimer, the term of this patent is extended or adjusted under 35 U.S.C. 154(b) by 322 days.

(21) Appl. No.: 15/381,346

(22) Filed: Dec. 16, 2016

(65) Prior Publication Data

US 2017/0321260 A1 Nov. 9, 2017

(30) Foreign Application Priority Data

May 9, 2016 (ES) .................................. 201630599

(51) Int. Cl.
*C12Q 1/68* (2018.01)
*C12Q 1/6827* (2018.01)
*C12Q 1/686* (2018.01)
*C12Q 1/6874* (2018.01)

(52) U.S. Cl.
CPC ........... *C12Q 1/6827* (2013.01); *C12Q 1/686* (2013.01); *C12Q 1/6874* (2013.01)

(58) Field of Classification Search
None
See application file for complete search history.

(56) References Cited

U.S. PATENT DOCUMENTS

| 2007/0148637 A1 | 6/2007 | Chang et al. |
| 2011/0306036 A1 | 12/2011 | Dauner et al. |
| 2013/0149695 A1 | 6/2013 | Lee et al. |

FOREIGN PATENT DOCUMENTS

GB 2364054 A 1/2002

OTHER PUBLICATIONS

Hutchison III, Clyde A. DNA sequencing: bench to bedside and beyond. Nucleic Acids Research 35:6227-6237. (Year: 2007).*
Agilent Technologies, Inc., "SureSelect$^{XT}$ Target Enrichment System for Illumina Paired-End Multiplexed Sequencing Library," Protocol Version B4, pp. 1-110, Aug. 2015.
Bick and Dimmock, "Whole exome and whole genome sequencing," *Curr Opin Pediatr.* 23:594-600, 2011.
Biesecker et al., "Exome sequencing: the expert view," *Genome Biol.* 12:128, 2011.
Hofacker et al., "Fast Folding and Comparison of RNA Secondary Structures," *Monatshefte für Chemie 125*:167-188, 1994.
Kent, "BLAT—The BLAST-Like Alignment Tool," *Genome Res.* 12:656-664, 2002.
Lai et al., "Comparative analysis of algorithms for identifying amplifications and deletions in array CGH data," *Genetics and Population Analysis 21*:3763-3770, 2005.
Reuter and Mathews, "RNAstructure: software for RNA secondary structure prediction and analysis," *BMC Bioinformatics 11*:129, 2010.
Stuppia et al., "Use of the MLPA Assay in the Molecular Diagnosis of Gene Copy Number Alterations in Human Genetic Diseases," *Int J Mol Sci. 13*:3245-3276, 2012.
Yoon et al., "Sensitive and accurate detection of copy number variants using read depth of coverage," *Genome Res. 19*:1586-1592, 2009.
Zhang et al., "Evaluation of copy number variation detection for a SNP array platform," *BMC Bioinformatics 15*:50, 2014.
Zhao et al., "Computational tools for copy number variation (CNV) detection using next-generation sequencing data: features and perspectives," *BMC Bioinformatics 14(Suppl 11)*:S1, 2013.
ES 201630599 Search Report dated Oct. 23, 2017 (6 pages).

* cited by examiner

*Primary Examiner* — Samuel C Woolwine
(74) *Attorney, Agent, or Firm* — Klarquist Sparkman, LLP

(57) ABSTRACT

The present invention relates to a method for identifying the position of a genetic mutation and to the use of said method for simplifying the screening of said genetic mutation.

20 Claims, 3 Drawing Sheets

Specification includes a Sequence Listing.

MUTATION IDENTIFICATION METHOD

CROSS REFERENCE TO RELATED APPLICATION

This application claims priority to Spanish Application No. P201630599 field May 9, 2016, herein incorporated by reference.

FIELD OF THE INVENTION

The present invention belongs to the field of molecular biology techniques. Specifically, it relates to a method for identifying the position of a genetic mutation and to the use of said method for simplifying the screening of said genetic mutation. The present invention is applicable in those fields which require precise knowledge of a genetic sequence or of the exact point of a genetic mutation (clinical practice, agronomy, biotechnology, etc.).

BACKGROUND OF THE INVENTION

The determination of sequences adjacent to a known region of the chromosome is a technically complicated task, and different methodologies have been developed to do this. The techniques that have been described include, among others, ligation-mediated PCR (LM-PCR or genome walking), inverse PCR (i-PCR), thermal asymmetric interlaced PCR (TAIL-PCR), anchored PCR (a-PCR) or randomly primed PCR (rm-PCR). All these methods suffer from low detection sensitivity or low specificity and are furthermore only effective when the point at which the mutation in the genome occurs is at most a few hundred base pairs away from the known sequence. More recently, other methodologies, such as linear amplification-mediated polymerase chain reaction (LAM PCR), which requires generating a double-stranded DNA fragment and digesting this fragment, have been developed. Subsequent modifications of this technique eliminate the need for this digestion, replacing it with the initial digestion of genomic DNA and the ligation of a double-stranded adapter. All these methods are based on exponential DNA amplification.

There are different well-established techniques for identifying regions of the genome with a loss or gain of genetic material. They include, among others, techniques based on PCR (multiplex ligation-dependent probe amplification, MLPA) or on hybridization (comparative genomic hybridization array (CGH array), single nucleotide polymorphism array (SNP array), etc.). Depending on the oligonucleotide or probe design, these techniques allow identifying regions of the genome in which the loss or gain of genetic material occurs, although in no case do they identify the exact start or end points of these regions, nor do they offer, in the case of insertions, any information about the region of the genome in which the insertion occurs. In the case of MLPA, this technique offers very low processivity given that only a limited number of genetic regions (normally exons) can be analyzed. Furthermore, it is a technique that leads to problems relating to the occurrence of false negatives.

In the case of SNP arrays and CGH array, the whole genome of the samples can be analyzed without prior knowledge about the sequence. However, it suffers from a relatively low resolution capacity since it is rarely capable of detecting deletions or insertions less than 50 Kb in size.

The use of techniques such as MLPA (Stuppia et al., *Use of the MLPA assay in the molecular diagnosis of gene copy number alterations in human genetic diseases*. Int J Mol Sci. 2012; 13: 3245-76), CGH array (Lai et al., *Comparative analysis of algorithms for identifying amplifications and deletions in array CGH data*. Bioinformatics 2005; 21: 3763-70), SNP arrays (Zhang et al., *Evaluation of copy number variation detection for a SNP array platform*. BMC Bioinformatics 2014; 15: 50) or NGS targeted sequencing (Zhao et al., *Computational tools for copy number variation (CNV) detection using next-generation sequencing data: features and perspectives*. BMC Bioinformatics 2013; 14 (Suppl 11): S1) allows detecting the presence of mutations due to the loss (deletions) or gain (insertions) of genetic material. The result obtained using any of these techniques delimits the minimal chromosomal region comprising with 100% certainty the structural variant, but none of them identifies the exact limits of the structural variant in question. That nucleic acid region comprising with 100% certainty a mutation in question is referred to hereinafter as the "ascertained nucleic acid region" or "ANA region."

Furthermore, there are other genetic modifications, such as translocations, that do not involve any change in the amount of genetic material and are therefore not detected with the mentioned methods. To detect the ANA region of these structural variants, specific techniques are used, such as Southern blot, karyotyping or fluorescence in situ hybridization (FISH) in translocations of large chromosome segments, or real time PCR (RT-PCR) or Δ-PCR for identifying other translocations which can give rise to gene fusions.

As regards gene fusions, it is currently considered that gene fusions, caused by chromosomal translocations, inversions, deletions, etc., are of great importance in common epithelial cancers, such as prostate or lung carcinomas. For example, most prostate cancers have a fusion that is regulated by androgens of one of the ETS gene family transcription factors. Clinically, some neoplasms are classified or managed according to the presence of a specific gene fusion: for example, promyelocytic leukemias carrying a PML-RARα fusion of retinoic acid α-receptor are treated with retinoic acid, whereas chronic myeloid leukemias with the presence of BCR-ABL fusion are treated with the drug imatinib. However, assays carried out using RT-PCR require knowing both fused elements which in turn give rise to a previously characterized variant, when sometimes only one of the genes which may be involved in the gene fusion is known. Said only one known gene would therefore correspond to the ANA region.

The recent emergence of massive ultrasequencing technologies (next generation sequencing, NGS) has allowed tremendous progress in knowledge about nucleic acid sequences of a wide range of organisms. This knowledge has in turn been used for showing the sources of genetic variability that often went unnoticed in the past, including, among others, genomic structural variants and copy-number variation (CNV).

There are different methods for preparing samples for NGS. In one of them, the methodology includes a "target enrichment" step, consisting of selecting, through different methods (for example, by means of capturing with a solution containing specific probes), that region of the genome to be studied (for example, for sequencing a panel of specific genes, for sequencing only exomes, etc.), disregarding the rest of the genome. These methods obtain extremely reliable readings from a region of interest but almost no information from the rest of the genome.

Another option for characterizing mutations of this type consists of performing whole genome sequencing (WGS) on those samples suspected of having modifications of this type. Although this methodology offers results covering the entire genome, there are recalcitrant areas in which there are few readings or none at all. Furthermore, the WGS methodology is expensive and presents problems when the region of interest is located in repetitive regions of the genome, so it does not assure the correct characterization of genetic variants of this type.

The authors of the present invention have developed a method that overcomes the problems of the aforementioned techniques and allows simplifying the method for identifying mutations and the screening of said mutations.

OBJECT OF THE INVENTION

In a first aspect, the present invention relates to a method for identifying the position of a genetic mutation characterized in that it comprises the following steps:
a) determining the ANA region comprising the genetic mutation under study;
b) carrying out a PCR, where the PCR template is DNA extracted from a biological sample taken from the subject under study, and the primers are:
  b1) a degenerate primer, and
  b2) a specific primer which hybridizes specifically:
    within the ANA region, at a distance of 0.2-100 Kb from any of the ends of the ANA region, if the mutation comprises a gain of genetic material, a translocation or a gene fusion, and is extended by means of PCR out of the ANA region, or
    outside the ANA region, at a distance of 0.2-100 Kb from any of the ends of the ANA region, if the mutation comprises a loss of genetic material, and is extended by means of PCR into the ANA region,
and where in the PCR reaction the hybridization step comprises two consecutive hybridizations, a first hybridization at a hybridization temperature equal to the Tm of the specific primer ±10° C., and a second hybridization at a hybridization temperature equal to the Tm of the degenerate primer ±5° C.;
c) sequencing the amplification product obtained in step b); and
d) aligning the sequence obtained in step c) with a reference genome for identifying the position of the mutation.

A second aspect of the present invention relates to a method for screening a genetic mutation, characterized in that it comprises the following steps:
i) identifying the position of the genetic mutation following the method according to the first aspect of the invention;
ii) carrying out a PCR where the DNA template is DNA extracted from a biological sample taken from the subject under study, and the primers are a forward primer and a reverse primer hybridizing specifically upstream and downstream, respectively, of the position of the mutation identified in step i) such that a PCR product comprising said position is amplified;
iii) analyzing the size of the PCR product amplified in ii), where a PCR product having the expected size according to the forward and reverse primers used in step ii) is indicative of the presence of the genetic mutation under study, and the absence of said PCR product is indicative of the absence of the genetic mutation.

A third aspect of the present invention relates to a method for the diagnosis of a genetic mutation-associated pathology which comprises carrying out the method according to the second aspect of the invention, the subject under study being diagnosed as having the pathology when the PCR product of step iii) has the expected size according to the forward and reverse primers used in step ii).

A fourth aspect of the present invention relates to a kit for carrying out any one of the methods according to the first aspect, second aspect or third aspect of the invention, comprising a degenerate primer b1) and a specific primer b2), as defined in the first aspect of the invention.

Figure 1:
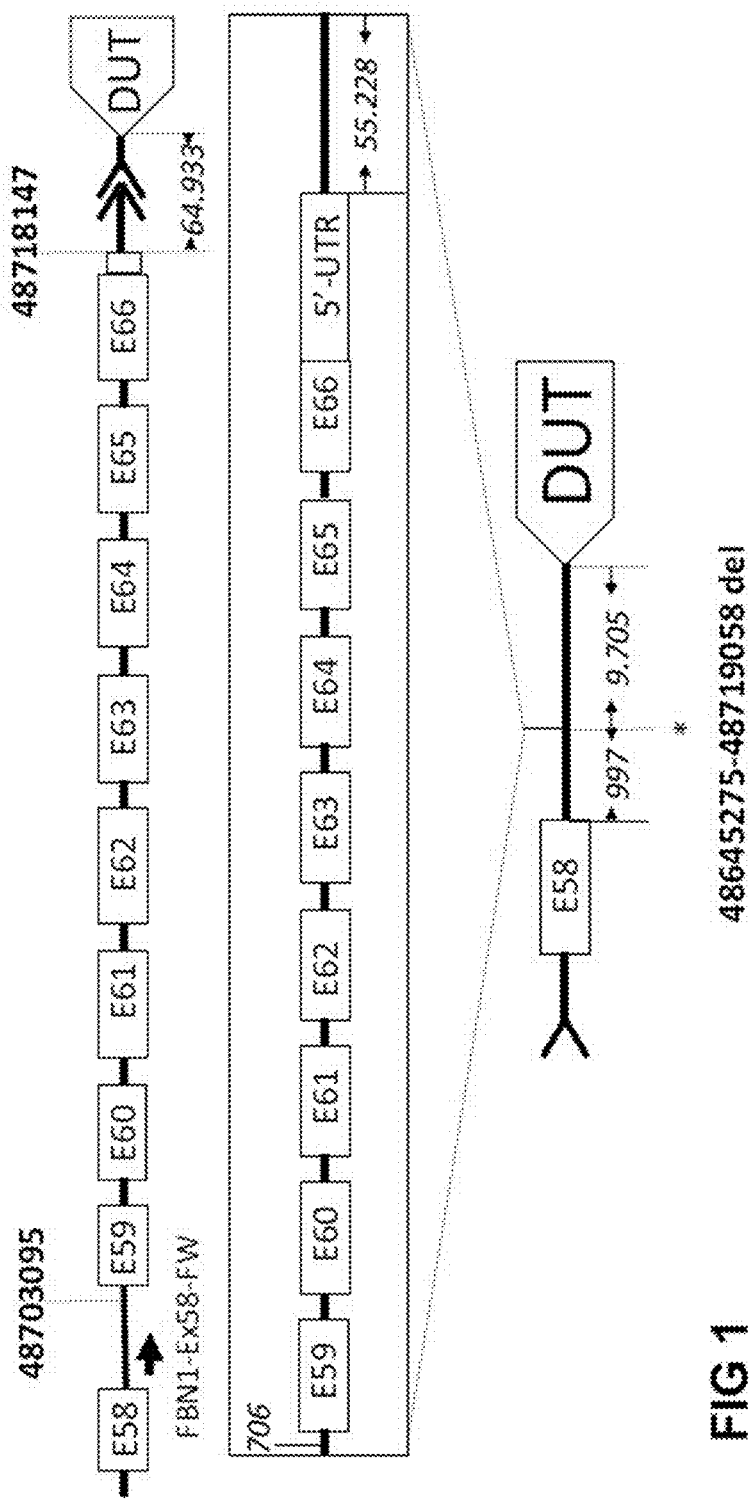
FIG. 1 shows a diagram of the deletion of exons 59-66 of the FBN1 gene. DUT refers to the deoxyuridine triphosphatase gene, adjacent to the FBN1 gene towards the centromere. The numbers indicated in italics represent the number of nucleotides. The numbers indicated in bold represent the position in the chromosome. The term "Eno." means "exon no.," for example "E58" means "exon 58." The FBN1-Ex58-FW arrow denotes the specific primer, the head of the arrow representing the extension direction of said primer.

The numbers indicated in italics represent the number of nucleotides. The numbers indicated in bold represent the position in the chromosome. The term "Eno." means "exon no.," for example E46 means Exon 46. The DMDdup-Ex47-RV arrow denotes the specific primer, the head of the arrow representing the extension direction of said primer.

Sequence Listing

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 14, 2016, 8 KB, which is incorporated by reference herein. In the accompanying sequence listing:

SEQ ID NO: 1 is the nucleotide sequence of a degenerate primer.
SEQ ID NO: 2 is the nucleotide sequence of primer FBN1-Ex58-FW.
SEQ ID NO: 3 is the nucleotide sequence of primer FBN1_del8-FW.
SEQ ID NO: 4 is the nucleotide sequence of primer FBN1_del8-RV.
SEQ ID NO: 5 is the nucleotide sequence of primer DMDdup-Ex47-RV.
SEQ ID NO: 6 is the nucleotide sequence of primer DMD_46-47dup-FW.
SEQ ID NO: 7 is the nucleotide sequence of primer DMD_46-47dup-RV.

DETAILED DESCRIPTION OF THE INVENTION

As used herein, the singular forms "a," "an" and "the" include their corresponding plural forms unless the context clearly indicates otherwise. Unless defined otherwise, all the technical and scientific terms used herein have the same meaning as commonly understood by a person skilled in the art to which this invention belongs. To facilitate understanding and clarify the meaning of specific terms in the context of the present invention, the following definitions and particular and preferred embodiments thereof, applicable to all the embodiments of the different aspects of the present invention, are provided:

"PCR" means polymerase chain reaction. It generally consists of the repetition of successive incubations at a denaturation temperature, a hybridization temperature and a polymerization temperature, although there are countless modifications to the general method. PCR-based methods, such as touchdown PCR (TD-PCR), nested PCR, first extension, etc., are included.

"Amplification product" or "PCR product" is the mixture of DNAs in solution obtained as a result of a PCR reaction.

"Primer" is an oligonucleotide which is capable of hybridizing with the sequence to be amplified and is used as a starting point for the polymerase to begin the amplification reaction. This molecule can include modifications, such as biotinylation, phosphorylation, or addition of locked nucleic acids (LNA).

"Specific primer" refers to a primer which is capable of binding specifically or hybridizing specifically with the sequence to be amplified. In a particular embodiment, the primer is a deoxyoligonucleotide with a size of 15-35 nucleotides, preferably 18-25 nucleotides.

"Hybridizing specifically" refers to the recognition between nucleic acid molecules having exact complementarity (100% complementarity) between their nucleotide sequences.

"Degenerate primer" refers to mixtures of oligonucleotides made up of nucleotides N (N is A, T, C or G). Particularly, the oligonucleotides are 5-16 nucleotides in length, preferably 5-11, and more preferably 7 nucleotides in length. In the oligonucleotides, all the Ns can be the same nucleotide or they can be different, the oligonucleotide therefore comprising variations in the sequence in any of its positions. It can particularly comprise variations in at least 1, at least 2, at least 3, at least 4, at least 5, at least 6, at least 7, at least 8, at least 9, at least 10, at least 11, at least 12, at least 13, at least 14, at least 15 positions, according to the size of the oligonucleotide. In a preferred embodiment, the degenerate primer comprises a mixture of all the possible oligonucleotides. In a preferred embodiment, the oligonucleotides are phosphorylated (phosphorylated degenerate primer), preferably mono-phosphorylated. The oligonucleotides are preferably 5' end phosphorylated (5' end phosphorylated degenerate primer).

"Forward primer" is the primer that is extended in the PCR from the start codon to the stop codon of the template DNA.

"Reverse primer" is the primer that is extended from the stop codon to the start codon of the template DNA.

"Reference genome" refers to a digital nucleic acid sequence, previously assembled as a representative example of the set of genes of a species.

"Hybridization step" refers to the PCR hybridization phase. This phase is also called an annealing, pairing or alignment phase. The annealing or melting temperature (Tm) depends on several factors and is relatively specific for each primer. Primer length and sequence are critical in designating amplification parameters, and a simple formula for calculating the Tm is as follows: Tm=4(G+C)+2(A+T), although many other formulas can also be used. In the case of a degenerate primer, Tm refers to the mean Tm of the mixture of oligonucleotides made up of nucleotides N.

"Structural variants" involve changes in some parts of the chromosomes instead of changes in the number of chromosomes or sets of chromosomes in the genome. There are four common types of mutations which result in structural variants: deletions and insertions, for example duplications (involving a change in the amount of DNA in a chromosome, loss and gain of genetic material, respectively), inversions (involving a change in the arrangement of a chromosomal segment) and translocations (involving a change in the location of a chromosomal segment which can give rise to gene fusions). In the present invention, the term "structural variant" comprises a structural variant selected from the group consisting of a structural variant characterized by (comprising) a loss of genetic material, a structural variant characterized by a gain of genetic material, a translocation, a gene fusion and combinations thereof.

"Loss of genetic material" refers to the existence of regions of the genome in which at least one of the alleles shows the disappearance of a DNA segment that does appear in said allele in the reference genome. This loss can give rise to changes in the phenotype.

"Gain of genetic material" refers to the existence of regions of the genome in which at least one of the alleles shows the insertion of a DNA segment that is absent in said allele in the reference genome. The inserted DNA segment can have an endogenous origin (duplications, pseudogenes, retrotransposons, etc.) or exogenous origin (transgenes, viral integration, etc.). This gain of genetic material can give rise to changes in the phenotype depending on the insertion site or on the sequence of the inserted element. In the context of the present invention, the term "insertion" refers to any of the structural variants entailing a gain of genetic material, particularly the structural variants mentioned in this paragraph: duplication, pseudogene, retrotransposon, transgene and viral integration.

"Translocation" refers to the reorganization of regions of the genome giving rise to the presence of a DNA segment in a region of the genome other than the region in which it is located in the reference genome. Translocation can give rise to changes in the phenotype depending on the insertion or cleavage site and on the sequence of the inserted element.

"Gene fusion" refers to the result of breaking and fusing a DNA segment which occurs in sequences contained in genes. It generally occurs as a result of translocation and can give rise to a chimeric protein-producing fused transcript. Gene fusion can give rise to changes in the phenotype depending on the genes affected by the reorganization.

"Ascertained nucleic acid region" (ANA region) refers to the nucleic acid region (sequence of contiguous nucleotides in a nucleic acid molecule) comprising with 100% certainty a genetic mutation under study. The ANA region can be determined based on the genetic material extracted from a biological sample taken from the subject under study, particularly, based on the DNA or RNA extracted from a biological sample taken from the subject under study, preferably DNA. As indicated above, the ANA region can be determined through a wide range of techniques known by the person skilled in the art. MLPA, CGH array, SNP array, NGS, Southern blot, karyotyping, FISH, RT-PCR and Δ-PCR stand out, among others. Likewise, the person skilled in the art knows how to determine the region comprising with 100% certainty the mutation under study (ANA region).

"Gene" includes not only regions encoding gene products but also regulatory regions, including, for example, promoters, terminator regions, translation regulatory sequences (such as ribosome binding sites and internal ribosome entry sites), enhancers, silencers, insulators, boundary elements, origins of replication, matrix binding sites and locus control regions. The term "gene" furthermore includes all the introns and other DNA sequences from splicing the mRNA transcript, together with variants resulting from alternative splicing sites. The term "gene" furthermore includes any portion of a gene, for example, any portion of the aforementioned regions.

"Subject" refers to any member of the Monera, Protista, Fungi, Plantae or Animalia kingdom. In a preferred embodiment, the subject is a member of the Magnoliophyta subdivision including, without limitation, model organisms such as *Arabidopsis thaliana* or rice, and monocotyledon and dicotyledon plant species with agronomic interest, such as wheat and other cereals, sunflower, cotton, soybean and other leguminous plants, ornamental plants, fruit trees, conifers and other crops.

In another preferred embodiment, the subject is any member of the Mammalia class, including, without limitation, human beings and non-human primates such as chimpanzees and other apes and species of monkeys; farm animals, such as cattle, sheep, pigs, goats and horses; domestic mammals such as dogs and cats; laboratory animals including rodents, such as mice, rats and guinea pigs, and the like. The term does not indicate the specific age or gender. Therefore, male or female adult and newborn subjects, as well as fetuses, are intended for being included within the scope of this term. The subject is preferably a human being.

Before carrying out any of the methods of the present invention, the presence of the mutation in the subject under study may be known, or the subject may be suspected of having the mutation, for example, based on clinical data, or it may be completely unknown whether or not the subject has the mutation.

The "biological sample" taken from a subject under study contains any biological material which allows nucleic acid extraction and is a material comprising genetic material from a subject or from a combination of subjects. In the present invention, the sample comprises genetic material from the subject under study. In a particular embodiment, the genetic material is DNA or RNA. DNA refers to any type of DNA, such as for example: genomic DNA (gDNA), mitochondrial DNA (mDNA), complementary DNA (cDNA), circular DNA (ciDNA). In a particular embodiment, the genetic material is gDNA, mDNA, cDNA or ciDNA. In a preferred embodiment, the DNA is genomic DNA or cDNA, preferably genomic DNA. Nucleic acid can be isolated from the sample using standard methods known by the person skilled in the art, such as those described in Sambrook et al. (Molecular Cloning: A Laboratory Manual, New York: Cold Spring Harbor Press, 1989). In a particular embodiment, the biological sample is fresh or fixed tissue obtained from biopsy or autopsy or a biological fluid. In a preferred embodiment of any of the methods of the present invention, the biological sample is a biological fluid, the method of the invention therefore being non-invasive, minimally invasive or less invasive than methods requiring a tissue sample taken by means of biopsy. The biological fluid is selected from the group consisting of saliva, blood, serum, plasma, urine, feces, ejaculate, bone marrow, buccal or buccal-pharyngeal discharge, pleural fluid, peritoneal fluid, pericardial fluid, cerebrospinal fluid, intra-articular fluid, amniotic fluid, and mixtures thereof. The biological fluid is preferably selected from blood, plasma, serum or saliva, more preferably the biological sample is blood or saliva. In an additional embodiment, the biological sample is a maternal sample including fetal DNA, thereby allowing prenatal analysis.

In a first aspect, the present invention relates to a method for identifying the position of a genetic mutation, characterized in that it comprises the following steps:
a) determining the ANA region comprising the mutation under study;
b) carrying out a PCR, where the PCR template is DNA extracted from a biological sample taken from the subject under study, and the primers are:
  b1) a degenerate primer, and
  b2) a specific primer which hybridizes specifically:
    within the ANA region, at a distance of 0.2-100 Kb from any of the ends of the ANA region, if the mutation comprises a gain of genetic material, a translocation or a gene fusion, and is extended by means of PCR (in a 5' to 3' direction) out of the ANA region, or
    outside the ANA region, at a distance of 0.2-100 Kb from any of the ends of said region, if the mutation comprises a loss of genetic material, and is extended by means of PCR (in a 5' to 3' direction) into the ANA region,
and where in the PCR reaction the hybridization step comprises two consecutive hybridizations, a first hybridization at a hybridization temperature equal to the Tm of the specific primer ±10° C., and a second hybridization at a hybridization temperature equal to the Tm of the degenerate primer ±5° C.;
c) sequencing the amplification product obtained in step b); and
d) aligning the sequence obtained in step c) with a reference sequence for identifying the position of the mutation.

The present invention relates to methods for characterizing genetic mutations, specifically for identifying the exact position of said genetic mutations, thereby delimiting the exact limits of said mutations, and for screening said mutations (detecting the presence of said mutations). The methods described herein can be used in the characterization of a range of genetic mutations. The mutations which can be characterized using the methods described in the present invention include, for example, an insertion, a deletion, a duplication and a reorganization (for example, a translocation or a gene fusion), as well as any combination thereof. The insertion can be the insertion of a transgene. The genetic mutation can be a germ line mutation or a somatic mutation.

Therefore in a particular embodiment, the genetic mutation is a structural variant, more particularly the structural variant is selected from the group consisting of a structural variant characterized by a loss of genetic material, a structural variant characterized by a gain of genetic material, a translocation, a gene fusion and combinations thereof. In a preferred embodiment, the structural variant is selected from the group consisting of insertion, deletion, duplication, transgene, translocation and gene fusion. More preferably, the structural variation is an insertion, duplication or deletion.

The mutation under study can be a recurrent mutation that has been associated with one or more types of diseases, such as familial cardiopathies, for example. In this case, step a) can be carried out in a particular region of the DNA, for example, the region comprising the pathology-associated genes or the coding region of the genome (the exome), which is only 1% of the genome but it is where 85% of all hereditary diseases are encoded (Bick and Dimmock. *Whole exome and whole genome sequencing*, Curr Opin Pediatr 2011; 23: 594-600; Biesecker et al. *Exome sequencing: the expert view*, Genome Biol 2011:12:128), thereby preventing whole genome analysis.

In a particular embodiment, step a) of the method of the invention is carried out based on genetic material extracted from a biological sample taken from the subject under study, more particularly said genetic material is DNA or RNA. Step a) can be carried out by any method known by the person skilled in the art which allows determining the ANA region, such as, for example: MLPA, CGH, SNP arrays, NGS, etc. Therefore, in a particular embodiment step a) is carried out by means of a technique selected from the group consisting of MLPA, CGH array, SNP arrays, NGS, Southern blot, karyotyping, FISH, RT-PCR and Δ-PCR. In a preferred embodiment according to any one of the preceding embodiments, step a) is carried out by means of MLPA, CGH array, SNP arrays, NGS, and more preferably by means of NGS. In a preferred embodiment according to any one of the embodiments of this paragraph, the genetic material is DNA.

In a particular embodiment according to any one of the preceding embodiments, in step b) the PCR template is gDNA, cDNA or ciDNA, preferably gDNA or cDNA, and more preferably gDNA. In the case of gene fusions, the PCR template is preferably cDNA.

In a preferred embodiment according to any one of the preceding embodiments, the degenerate primer has between 5 and 11 nucleotides, and more preferably 7 nucleotides. The degenerate primer preferably has the sequence SEQ ID NO 1 (NNNNNNN). The degenerate primer can comprise modified nucleotides, for example, locked nucleic acids (LNAs). Likewise, the degenerate primer can be mono-, di- or tri-phosphorylated. In a preferred embodiment according to any one of the preceding embodiments of the first aspect of the invention, the degenerate primer is 5' end phosphorylated, preferably mono-phosphorylated. In a preferred embodiment, the degenerate primer has the sequence SEQ ID NO 1 and is 5' end phosphorylated (5'-pNNNNNNN-3').

In a particular embodiment according to any one of the preceding embodiments, in step b) the hybridization temperature of the second hybridization is between 20-40° C., preferably 27-33° C., and more preferably 30° C.

In another particular embodiment according to any one of the preceding embodiments, in step b) the second hybridization is carried out for a time between 1 and 10 seconds, preferably 1-3 seconds, and more preferably 1 second. Advantageously, the short hybridization limits the incorporation of degenerate oligonucleotides in the newly synthesized strands and prevents the appearance of non-specific reaction products.

In a preferred embodiment according to any one of the preceding embodiments, in step b) the second hybridization is carried out at 30° C. for 1 second, thereby achieving amplification with the smallest amount of non-specific reaction products.

Figures 2A, 2B:
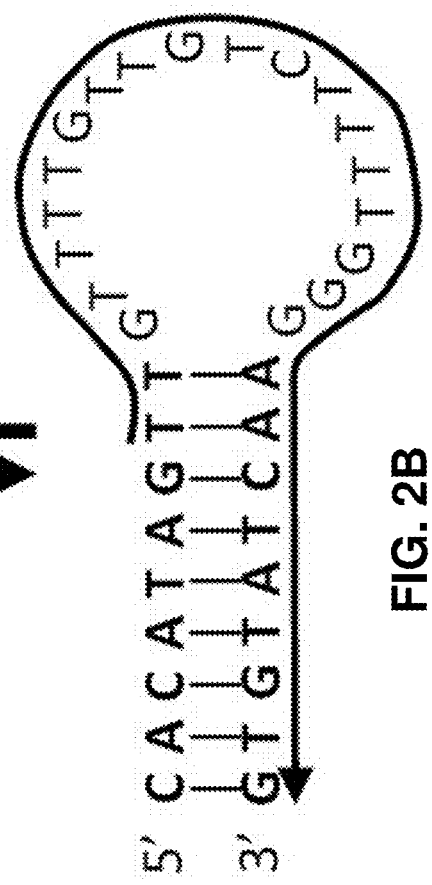
FIGS. 2A and 2B show a diagram showing the prediction of the secondary structure of the specific primer of SEQ ID NO 5 at 30° C. (B). (A) shows the structure at 60° C., where the arrow marks the region of homology with intron 45 of the DMD gene.

The PCR reaction therefore includes a step of hybridization at a low temperature and for a very short time to allow incorporating degenerate primers into the newly synthesized strands. To that end, and to reduce or prevent the specific primer from binding at that low temperature to other regions of the genome, the specific primer can include at its 5' end a sequence complementary to the sequence of its 3' end. This favors the formation of hairpin structures due to the hybridization between both ends of the primer at low annealing temperatures. This thereby reduces the possibility of non-specific homology of the specific primer with the DNA under study during the low-temperature annealing step (second hybridization). FIG. 2 shows the predicted secondary structure at 30° C. (panel B) for a specific primer in which a 7-nucleotide extension has been designed at its 5' end favoring the formation of intramolecular structures through the complementation of 9 nucleotides. The size of this region with complementation can vary depending on the GC content of the primer, but always so that it forms secondary structures at the hybridization temperature of the second hybridization which are not stable at the hybridization temperature of the first hybridization.

In a preferred embodiment according to any one of the preceding embodiments, the specific primer comprises at the 5' end a sequence complementary to the sequence of the 3' end thereof, having preferably 5-12 nucleotides and more preferably 7-9 nucleotides. The formation of secondary hairpin structures at low hybridization temperatures, such as the temperatures required for degenerate primer hybridization, is thereby favored, reducing the possibility of non-specific homology with the DNA under study.

In a particular embodiment according to any one of the preceding embodiments, the specific primer has the sequence SEQ ID NO 2 or SEQ ID NO 5.

As indicated above, the specific primer is designed such that it hybridizes specifically within or outside the ANA region according to the type of mutation being characterized. Said primer is extended by means of PCR in the 5' to 3' direction towards the position of the mutation under study. Therefore, in the case in which the mutation comprises a gain of genetic material, translocation or gene fusion, where the mutation is outside ANA, the specific primer hybridizes within the ANA region and is extended out of the ANA region. In the case in which the mutation comprises a loss of genetic material, the specific primer hybridizes outside the ANA region and is extended into the ANA region. In particular, the specific primer hybridizes specifically in a region located at 0.2-100 Kb from any of the ends (3' or 5') of the ANA region, within or outside the ANA region according to the mutation (within the ANA region in mutations comprising gain of genetic material, translocations or gene fusions and outside the ANA region in mutations comprising the loss of genetic material). More particularly, the specific primer hybridizes specifically at 0.5-80 Kb from the ends of the ANA region, preferably at 0.5-40 Kb, and more preferably at 0.5-20 Kb from the ends of the ANA region.

In a preferred embodiment, when the mutation is a structural variant characterized by a gain of genetic material, the specific primer hybridizes at 0.2-10 Kb from the 5' or 3' end, within the ANA region with the gain of genetic material.

In the present invention, in step b) the PCR is carried out with only primers b1) and b2). As a result of using a single specific primer, a linear amplification is obtained. Furthermore, in the preferred embodiment in which the degenerate primer is phosphorylated, the incorporation of said phosphorylated degenerate primer to the reaction allows priming the linear strands and generating local double-stranded regions on which the polymerase regenerates a double-stranded nucleic acid. That is a significant advantage since the methods established for preparing samples for NGS use double-stranded DNA as starting material. Therefore, in a preferred embodiment according to any one of the preceding embodiments, the sequencing of step c) is carried out by means of NGS. Furthermore, in another preferred embodiment according to any one of the preceding embodiments, in step b) the degenerate primer is 5' end phosphorylated, preferably mono-phosphorylated, and the sequencing of step c) is carried out by means of NGS.

In a particular embodiment, the method of the first aspect of the invention comprises, after step d) in which the position of the mutation is identified, a step e) which consist of designing primers flanking the position of the genetic mutation, carrying out a PCR reaction with said primers and DNA extracted from a biological sample of the subject under study and Sanger sequencing of the amplified product. Step e) therefore comprises reconfirming the position identified in step d) by means of Sanger sequencing. Sequencing using the method described by Sanger et al. in 1977 (Sanger et al., *DNA sequencing with chain-terminating inhibitors*. Proc Natl Acad Sci USA 1977; 74: 5463-7) is a clinical standard, so this step is advisable when the method of the invention is used for detecting or diagnosing diseases characterized by the genetic mutation under study.

Genetic abnormalities, such as duplication, deletion, chromosomal translocation, gene fusion and point mutation, often lead to pathological conditions. Some diseases, such as cancer, are the result of genetic abnormalities acquired in a few cells throughout life, whereas in other diseases the genetic abnormality is present in all the cells of the body since conception, as occurs in some familial cardiopathies. Therefore, in a particular embodiment the genetic mutation under study is a mutation which is associated with the development of a pathology, such as, for example, cardiopathies, cancer, neurological development disorders, Crohn's disease, rheumatoid arthritis, type 1 and type 2 diabetes, etc. In a preferred embodiment, the pathology is familial cardiopathy, more preferably cardiomyopathy or channelopathy.

In a particular embodiment according to any one of the preceding embodiments, the mutation is a deletion. More particularly, the deletion is that of a gene the deletion of which is associated with a pathology, preferably familial cardiopathy.

In a particular embodiment according to any one of the preceding embodiments, the mutation is an insertion. More particularly, the insertion is a duplication of at least one gene or at least one part of a gene and said duplication is associated with a pathology, preferably familial cardiopathy.

In a particular embodiment, the mutation is a deletion in the FBN1 gene and the specific primer has the sequence SEQ ID NO 2. In another particular embodiment, the mutation is a duplication of the DMD gene and the specific primer has the sequence SEQ ID NO 5. The deletion of the FBN1 gene is associated with Marfan syndrome and the duplication of the DMD gene is associated with muscular dystrophy and dilated cardiomyopathy.

The methodology of the present invention according to the first aspect of the invention allows knowing the sequence of regions spanning up to several tens of kilobases from a known sequence, with greater extension and specificity than the methods previously described in the state of the art. To carry out the method of the invention, having a known sequence on the basis of which a single specific oligonucleotide is designed is sufficient and no prior knowledge about the sequence to be characterized is required.

As indicated above, the methods of the state of the art are based on exponential DNA amplification. Surprisingly, the method of the present invention eliminates the need for this step and integrates in the PCR reaction an additional reagent which regenerates the double strand without having to add adaptors. The need to synthesize oligonucleotides with modifications which favor PCR product capture (for example, biotinylation) is furthermore eliminated since the sequencing of step c), particularly by means of NGS, provides the sensitivity required for identifying DNA fragments covering the exact limits of the genetic modification. Therefore, in a preferred embodiment according to any one of the preceding embodiments according to the first aspect of the invention, the specific primer does not comprise modifications.

The method of the present invention is therefore of special interest for applying it to samples from subjects in which, after applying one or more of the techniques mentioned in the background of the invention section or others, the loss or gain of genetic material is identified. Applying this invention allows accurately characterizing the exact limits of the deletion, insertion, translocation or gene fusion, and in the case of insertion, translocation and gene fusion, determining the exact location in the genome in which it occurs.

The invention is also applicable in the characterization of transgene insertion sites in organisms in which a known exogenous sequence is introduced in the genome by means of genetic manipulation.

The invention is also applicable in the characterization of gene fusions. Surprisingly, and unlike the techniques in use, the present invention serves for the identification and characterization of fusions based on the sequence of only one of the genes involved in the fusion. For example, the assays which can be carried out using RT-PCR to detect gene fusions require knowing both fused elements which in turn give rise to a previously characterized variant. In the present invention, gene fusion can be characterized based on the only one known gene involved in said gene fusion. In this case, the ANA region corresponds to said only one known gene. The present invention therefore entails a significant advantage, since as indicated above, it is currently considered that gene fusions caused by chromosomal translocations, inversions, deletions, etc., are of great importance in common epithelial cancers, such as prostate or lung carcinomas.

Once the position of the mutation has been identified following the method of the first aspect of the present invention, it is possible to design primers which allow specifically amplifying the exact point of the mutation. Furthermore, once these primers are available, the study of the presence or absence of the mutation in related individuals is limited to PCR and Sanger sequencing, which has been an established method for years now and is much more cost-effective and less technically demanding than NGS. Therefore, in a second aspect the present invention relates to a method for screening a genetic mutation characterized in that it comprises the following steps:

i) identifying the position of the genetic mutation following the method of the invention according to any one of the embodiments of the first aspect of the invention;

ii) carrying out a PCR where the DNA template is DNA extracted from a sample taken from a subject under study and the primers are a forward primer and a reverse primer hybridizing specifically upstream and downstream, respectively, of the exact position of the mutation such that a PCR product comprising said position is amplified;

iii) analyzing the size of the PCR product amplified in ii), where a PCR product having the expected size according to the forward and reverse primers of step ii) (i.e., expected size according to the position in which said primers hybridize) is indicative of the presence of the genetic mutation, and the absence of said PCR product with the expected size is indicative of the absence of the genetic mutation.

In a particular embodiment of the second aspect of the invention according to any one of the preceding embodiments, when the analysis of step iii) indicates the presence of the genetic mutation, the method further comprises a step iv) in which the PCR product obtained in step ii) is sequenced.

In another particular embodiment of the second aspect of the invention according to any one of the preceding embodiments, alternatively to step iii), a step iv) is carried out, in which the PCR product obtained in step ii) is sequenced. In this case, the result of the sequencing will show the presence or absence of the genetic mutation under study.

In a preferred embodiment according to any one of the particular embodiments of the two preceding paragraphs, the product obtained in step ii) is purified and concentrated before being sequenced in step iv). In a preferred embodiment, the sequencing of step iv) is Sanger sequencing which is a clinical standard sequencing, as indicated above.

As indicated above, many genetic mutations which can be characterized by the methods of the present invention are associated with pathologies. Therefore, in a particular embodiment according to any one of the embodiments of the second aspect of the invention, the genetic mutation is associated with a pathology, such as for example, cardiopathies, cancer, neurological development disorders, Crohn's disease, rheumatoid arthritis, type 1 and type 2 diabetes, etc. In a preferred embodiment, the pathology is familial cardiopathy, more preferably cardiomyopathy or channelopathy.

Given that the method according to the second aspect of the present invention allows determining the presence or absence of a mutation and said mutation can be associated with a pathology, said method can be used in the diagnosis of said pathology. Therefore, in a third aspect the present invention relates to a method for the diagnosis of a given genetic mutation-associated pathology comprising the steps of the method according to any one of the embodiments of the second aspect of the invention in which step iii) is carried out, the subject under study being diagnosed as having the pathology when the PCR product of step iii) has the expected size according to the forward and reverse primers used in step ii).

The third aspect of the invention also relates to a method for the diagnosis of a given genetic mutation-associated pathology comprising the steps of the method according to any one of the embodiments of the second aspect of the invention in which step iv) is carried out instead of step iii), the subject under study being diagnosed as having the pathology when the sequencing of step iv) shows the presence of the genetic mutation.

The third aspect of the invention also relates to the use of a method according to any one of the embodiments of the first or second aspect of the present invention for the diagnosis of a genetic mutation-associated pathology.

In a preferred embodiment according to any of the embodiments of the third aspect of the invention, the pathology is selected from the group consisting of cardiopathies, cancer, neurological development disorders, Crohn's disease, rheumatoid arthritis, type 1 diabetes and type 2 diabetes. In a preferred embodiment, the pathology is familial cardiopathy, more preferably cardiomyopathy or channelopathy. In another preferred embodiment, the pathology is selected from the group consisting of Marfan syndrome, muscular dystrophy and dilated cardiomyopathy.

Other applications or uses of the methods of the present invention include the identification of a haplotype sequence along a segment of the chromosome (such as, for example, for determining the origin of various mutations in the case of compound heterozygotes), or the determination of DNA insertion points in biological materials used in gene therapy, transgenic organism production, etc.

Finally, in a fourth aspect the present invention relates to a kit for carrying out the method according to the first, second or third aspects, comprising:
 a degenerate primer b1), as defined in any of the particular embodiments of the first aspect of the invention, preferably having the sequence SEQ ID NO 1,
 a specific primer b2) as defined in the first aspect of the invention, preferably having the sequence SEQ ID NO 2 or SEQ ID NO 5.

In a preferred embodiment according to any one of the embodiments of the preceding paragraph, the degenerate primer is a 5' end phosphorylated degenerate primer.

EXAMPLES

Specific embodiments of the invention that serve to illustrate the invention without limiting the scope thereof are described in detail below.

Example 1

Characterization of the Deletion of Exons 59-66 of the FBN1 Gene 1.1. Identification of the ANA Region—Loss of Genetic Material (Deletion)

DNA was extracted from 1 mL of blood in a QIAsymphony SP automatic nucleic acid extractor (QIAGEN) using the QIAsymphony DSP DNA Midi Kit.

Samples were obtained from different subjects, specifically, the subject under study and other subjects without the cardiopathy under study. Mutations in the FBN1 gene are associated with the development of Marfan syndrome, a pathology which is consistent with the clinical data of the subject under study.

The samples were prepared using the SureSelectXT Target Enrichment System for Illumina Paired-End Multiplexed Sequencing Library kit (Agilent, SureSelectXT Target Enrichment System for Illumina Paired-End Multiplexed Sequencing Library Protocol Version B4, August 2015 SureSelect platform manufactured with Agilent SurePrint Technology), by hybridization with a solution containing probes homologous to the exon region having 214 genes, and they were sequenced in HiSeq 1500 equipment (Illumina). The comparison of the depth of coverage between samples sequenced at the same time (Yoon et al., *Sensitive and accurate detection of copy number variants using read depth of coverage*. Genome Res. 2009; 19: 1586-92) allowed identifying the deletion of the last 8 exons (exons 59-66) of the FBN1 gene in one of the DNA samples. The deletion started at an undetermined point of intron 58 and extended to the intergenic region downstream of the FBN1 gene (ANA region=chr15:48703095-48718147; reference genome hg19). The ANA region therefore comprises exons 59-66 of the FBN1 gene.

Mutations in this gene are associated with the development of Marfan syndrome, a pathology which is consistent with the clinical data of the subject under DNA study. The deletion extends to the intergenic region, into an area not covered by the enrichment method used in the sample preparation. Therefore, the deletion could span from 14 Kb to 6 Mb (distance at which the closest gene present in the enriched region is located). The method of the invention is used for characterizing the exact range of the mutation.

1.2. Amplification
1.2.1. Composition of the PCR Reaction:

| | |
|---|---|
| 10X Long PCR buffer with 15 mM MgCl$_2$ | 5 µL |
| dNTP Mix, 2 mM each | 5 µl (0.2 mM each). |
| Specific primer FBN1-Ex58-FW | 1 µM |
| DNA template | 50 ng |
| N7* | 0.2 µM |
| Long PCR enzyme (Thermo Scientific, K0181) | 2.5 U |
| Nuclease-free H$_2$0 | up to 50 µL |

(*): N7 = mixture of 5' phosphorylated degenerate primers (5' end phosphorylated SEQ ID NO 1: 5'-pNNNNNNNN-3').
Primer FBN1-Ex58-FW: GCTTTCCCCTCTTGCTTCTTCT (SEQ ID NO 2), hybridizes outside the ANA region and is extended into the ANA region.

1.2.2. PCR Reaction Conditions:
3 min, 94° C.;
10 cycles [94° C., 20 s; 60° C. 30 s; 30° C., 1 s; 68° C., 20 min];
25 cycles [94° C., 20 s; 60° C.; 30 s 30° C., 1 s; 68° C., 20 min, with an extension of 15 s per cycle]
Final extension of 10 min at 68° C.
These are optimized PCR conditions and reaction mixture for amplifying 30 Kb.

1.3. Preparation of the Amplification Products for Sequencing:
1.3.1. Elimination of primers and low molecular weight fragments using Agencourt AMPure XP (Beckman Coulter, A63881) following the manufacturer's instructions.
1.3.2. Preparation of libraries with NEXTflex™ Rapid DNA Sequencing Kit (Bioo Scientific, 5144-02) and NEXTflex™ DNA Barcodes-96 Kit (Bioo Scientific, 514105) following the manufacturer's instructions.
1.3.3. Sample quantification and preparation of a pool for sequencing the libraries.

1.4. Library NGS:
NGS was performed in an Illumina Hi-Seq 1500 ultra-sequencer. Sequencing was carried out in rapid mode and paired-end format at 2×100 (HISEQ Rapid SBS Kit v2).

1.5. Bioinformatics Analysis
Library demultiplexing was performed with CASAVA 1.8.2 software (Illumina). The files corresponding to each sample (in Fastq format) were aligned against the reference human sequence GRCh37/hg19 using the BWA-MEM computer program.
This analysis allowed detecting several non-duplicated chimeric sequences located upstream of the deletion (FIG. 1). The comparison of these chimeric sequences with the reference genome using the BLAT tool (UCSC Genome Browser) showed that said sequences included, covering both ends, an apparent deletion of ~73.8 Kb (FIG. 1).

1.6. Confirmation and Screening
To confirm that said deletion was real, oligonucleotides were designed and synthesized at both 3' and 5' ends of the deletion. A PCR reaction on the DNA of the sample showing the deletion with the forward primer (FBN1_del8-FW) and reverse primer (FBN1_del8-RV) having the sequences SEQ ID NO 3 (TGGAAAAGCACAAGCTCCTT) and SEQ ID NO 4 (CCAGGCAAGTGTCAGCATTA), respectively, produced a ~500 bp amplicon that was not observed in control samples. This amplicon was sequenced by means of Sanger sequencing and the presence of a deletion with coordinates NC_000015.9:g.48645275_48719058del was confirmed (marked with * in FIG. 1).

The study of the possible presence of the mutation in samples from family members of the subject under study is thereby simplified to analyzing the amplicon obtained from the primers flanking the deletion, such as the oligonucleotides having SEQ ID NO 3 and SEQ ID NO 4, for example.

Example 2

Characterization of the Duplication of Exons 46 and 47 of the DMD Gene 2.1. Identification of the ANA Region—Gain of Genetic Material (Insertion)
This was carried out similarly to section 1.1, but the duplication of exons 46 and 47 and of part of the adjacent introns of the DMD gene was analyzed. Mutations in this gene are associated with the development of muscular dystrophy and dilated cardiomyopathy, a pathology that is consistent with the clinical data of the DNA donor. The duplication includes exons 46 and 47 in their entirety and part of introns 45 and 47, but not exons 45 or 48 (ANA region=chrX:31946705-31951957; reference genome, hg19), so it could span from 5.2 Kb to 100 Kb. No information about the point of insertion in the genome is obtained. The method of the invention is used for characterizing the exact range and location of the mutation.

2.2. Amplification
In this case, an oligonucleotide is designed which includes in its 5' region a sequence complementary to the sequence of the 3' end to minimize the possibility of non-specific hybridization at low annealing temperatures (second hybridization).
The following specific primer is used:

DMDdup-Ex47-RV
(SEQ ID NO 5)
5'-CACATAGTTGTTTTGTTGTCTTTTGGGAACTATGTG.

The underlined sequence (positions 8-36 of the primer) is complementary to coordinates NC_000023.10:g. 31951631-31951659, contained in the duplicated area. Positions 1-9 of the oligonucleotide are complementary to positions 28-36 (both indicated in bold). According to different models (RNAstructure: Reuter & Mathews, *RNAstructure: Software for RNA secondary structure prediction and analysis*. BMC Bioinformatics 2010; 11: 129; RNAfold: Hofacker et al., *Fast folding and comparison of RNA secondary structures*. Monatsh Chemie 1994; 125: 167-8), it is predicted that this primer has a secondary structure at 30° C. (temperature of the second hybridization) (see FIG. 2). The same programs predict the absence of a secondary structure at 60° C. (temperature of the first hybridization).

The PCR reaction was the same (with the exception of the specific primer) as in Example 1 and was carried out in the same conditions as in Example 1.

2.3-2.5

Amplification product preparation, NGS and bioinformatics analysis were carried out as explained in Example 1.

Figure 3:
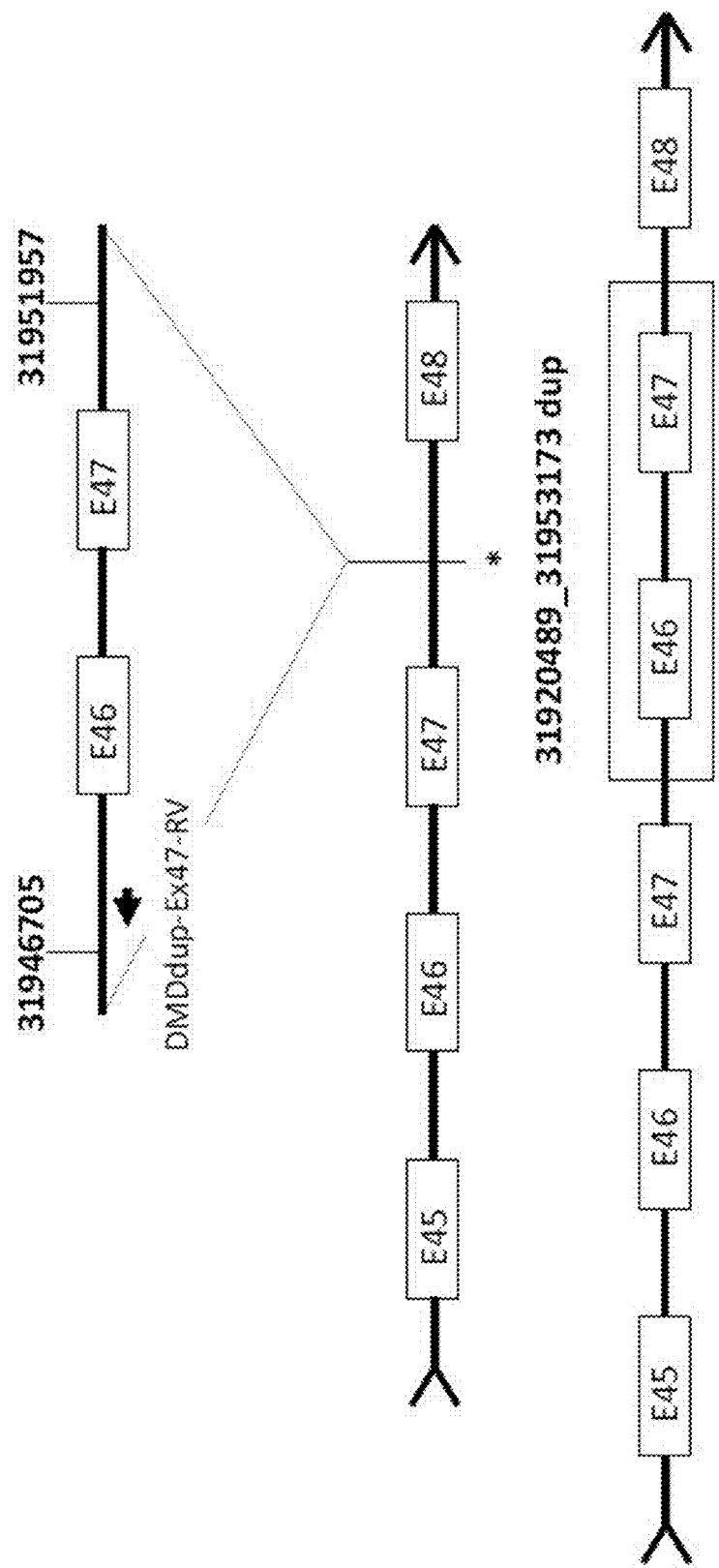
FIG. 3 shows a diagram of the duplication of exons 46 and 47 of the DMD gene.

The analysis allowed detecting non-duplicated paired sequences (identified by paired-end sequencing) that are compatible with the presence of a tandem duplication (FIG. 3). The comparison of these sequences with the reference genome using the BLAT tool (Kent, *BLAT—the BLAST-like alignment tool*. Genome Res 2002; 12: 656-64. UCSC Genome Browser) suggested that said sequences spanned the ends of a possible tandem duplication of ~32.4 Kb, which includes DMD exons 46 and 47 (FIG. 3).

2.6. Confirmation and Screening

To confirm that said duplication was real, primers were designed and synthesized at both ends of the possible duplicated region. A PCR reaction on the DNA of the sample showing duplication with oligonucleotides DMD_46-47dup-FW of SEQ ID NO 6 (CAGTTGGCAGA-GAAAACACG) and DMD_46-47dup-RV of SEQ ID NO 7 (TATCGCTTTGCCTACGCTCT) produced a ~500 bp amplicon that was not observed in control samples. This amplicon was sequenced by means of Sanger sequencing and the presence of a tandem duplication of the chromosomal region corresponding to the coordinates NC_000023.10: g.31920489_31953173 dup was confirmed.

The study of the possible presence of the mutation in samples from family members of the subject under study is thereby simplified to analyzing the amplicon obtained from primers having SEQ ID NO 6 and 7 flanking the duplication insertion point.

---

The invention claimed is:

1. A method for identifying the position of a genetic mutation, comprising:
   a) determining an ascertained nucleic acid (ANA) region comprising the genetic mutation;
   b) performing polymerase chain reaction (PCR) with primers to generate a PCR product, wherein the PCR template is DNA extracted from a biological sample obtained from a subject, and the primers are:
   b1) a degenerate primer, and
   b2) a specific primer:
      hybridizing specifically within the ANA region, at a distance of 0.2-100 Kb from any end of the ANA region, if the genetic mutation comprises a gain of genetic material, a translocation or a gene fusion, and extending by PCR out of the ANA region, or
      hybridizing specifically outside the ANA region, at a distance of 0.2-100 Kb from any end of the ANA region, if the mutation comprises a loss of genetic material, and extending by PCR into the ANA region,
   and wherein in the PCR, the hybridizing comprises two consecutive hybridizations, a first hybridization at a hybridization temperature equal to the Tm of the specific primer ±10° C., and a second hybridization at a hybridization temperature equal to the Tm of the degenerate primer ±5° C.;
   c) sequencing the PCR product obtained in step b) to obtain a sequence; and
   d) aligning the sequence obtained in step c) with a reference genome for identifying the position of the genetic mutation.

2. The method of claim 1, wherein step a) is performed based on DNA or RNA extracted from a biological sample obtained from the subject.

3. The method of claim 1, wherein step a) is performed on DNA by multiplex ligation-dependent probe amplification (MLPA), comparative genomic hybridization (CGH) array, single nucleotide polymorphism (SNP) array, next generation sequencing (NGS), Southern blot, karyotyping, fluorescence in situ hybridization (FISH), RT-PCR or Δ-PCR.

4. The method of claim 1, wherein in the PCR template is gDNA, cDNA or ciDNA.

5. The method of claim 1, wherein the degenerate primer is a 5' end phosphorylated degenerate primer.

6. The method of claim 1, wherein the specific primer comprises at its 5' end a sequence complementary to a sequence of its 3' end.

7. The method of claim 1, wherein the degenerate primer has between 5 and 16 nucleotides.

8. The method of claim 1, wherein the hybridization temperature of the second hybridization is between 20-40° C.

9. The method of claim 1, wherein the second hybridization is performed for 1 to 10 seconds.

10. The method of claim 1, wherein the specific primer hybridizes at 0.5-80 Kb from the 3' or 5' end of the ANA region.

11. The method of claim 1, wherein the degenerate primer has the sequence shown in SEQ ID NO 1.

12. The method of claim 1, wherein the sequencing of step c) is performed by next generation sequencing (NGS).

13. The method of claim 1, wherein after step d), in which the position of the mutation is identified, further comprising step e) comprising reconfirming the position of the mutation by Sanger sequencing.

14. The method of claim 1, wherein the genetic mutation is selected from the group consisting of insertion, deletion, duplication, transgene, translocation and gene fusion.

15. A method for screening a genetic mutation, comprising:

i) identifying the position of a genetic mutation using the method of claim 1;

ii) performing PCR to generate another PCR product, wherein the PCR template is DNA extracted from a sample obtained from a subject, and the primers are a forward primer and a reverse primer hybridizing specifically upstream and downstream, respectively, of the exact position of the genetic mutation;

iii) analyzing the size of the PCR product amplified in ii), wherein a PCR product having the expected size according to the forward and reverse primers of step ii) is indicative of the presence of the genetic mutation, and the absence of said PCR product is indicative of the absence of the genetic mutation.

16. The method of claim 15, further comprising after step iii) a step iv) comprising sequencing the PCR product obtained in step ii).

17. A method for screening a genetic mutation, comprising:

i) identifying the position of a genetic mutation using the method of claim 1;

ii) performing PCR to generate another PCR product, wherein the PCR template is DNA extracted from a sample obtained from a subject; and the primers are a forward primer and a reverse primer hybridizing specifically upstream and downstream, respectively, of the exact position of the genetic mutation; and iii) sequencing the PCR product obtained in step ii), wherein the result of the sequencing shows the presence or absence of the genetic mutation.

18. The method of claim 15, wherein the subject is diagnosed as having a genetic mutation-associated pathology when the PCR product of step iii) has the expected size according to the forward and reverse primers used in step ii).

19. The method of claim 17, wherein the subject is diagnosed as having a genetic mutation-associated pathology when the sequencing of step iii) shows the presence of the genetic mutation.

20. The method of claim 1, wherein the biological sample is selected from the group consisting of fresh or fixed tissue obtained from biopsy or autopsy, blood, plasma, serum, urine, feces, saliva, ejaculate, bone marrow, cerebrospinal fluid, ascitic fluid, synovial fluid, amniotic fluid, buccal or buccal-pharyngeal discharge, pleural fluid, peritoneal fluid, pericardial fluid, intra-articular fluid, and mixtures thereof.

* * * * *

SEQUENCE LISTING

```
<160> NUMBER OF SEQ ID NOS: 7

<210> SEQ ID NO 1
<211> LENGTH: 7
<212> TYPE: DNA
<213> ORGANISM: Artificial Sequence
<220> FEATURE:
<223> OTHER INFORMATION: Degenerate primer
<220> FEATURE:
<221> NAME/KEY: misc_feature
<222> LOCATION: (1)..(7)
<223> OTHER INFORMATION: n is a, c, g, or t

<400> SEQUENCE: 1 nnnnnnn                                                                    7

<210> SEQ ID NO 2
<211> LENGTH: 22
<212> TYPE: DNA
<213> ORGANISM: Artificial Sequence
<220> FEATURE:
<223> OTHER INFORMATION: FBN1-Ex58-FW primer

<400> SEQUENCE: 2
gctttcccct cttgcttctt ct                                                  22

<210> SEQ ID NO 3
<211> LENGTH: 20
<212> TYPE: DNA
<213> ORGANISM: Artificial Sequence
<220> FEATURE:
<223> OTHER INFORMATION: FBN1_del8-FW primer

<400> SEQUENCE: 3
tggaaaagca caagctcctt                                                     20

<210> SEQ ID NO 4
<211> LENGTH: 20
<212> TYPE: DNA
<213> ORGANISM: Artificial Sequence
<220> FEATURE:
<223> OTHER INFORMATION: FBN1_del8-RV primer

<400> SEQUENCE: 4
ccaggcaagt gtcagcatta                                                     20

<210> SEQ ID NO 5
```

```
<211> LENGTH: 36
<212> TYPE: DNA
<213> ORGANISM: Artificial Sequence
<220> FEATURE:
<223> OTHER INFORMATION: DMDdup-Ex47-RV primer

<400> SEQUENCE: 5
cacatagttg ttttgttgtc ttttgggaac tatgtg                              36

<210> SEQ ID NO 6
<211> LENGTH: 20
<212> TYPE: DNA
<213> ORGANISM: Artificial Sequence
<220> FEATURE:
<223> OTHER INFORMATION: DMD_46-47dup-FW primer

<400> SEQUENCE: 6
cagttggcag agaaaacacg                                                20

<210> SEQ ID NO 7
<211> LENGTH: 20
<212> TYPE: DNA
<213> ORGANISM: Artificial Sequence
<220> FEATURE:
<223> OTHER INFORMATION: DMD_46-47dup-RV primer

<400> SEQUENCE: 7
tatcgctttg cctacgctct                                                20
```